(12) United States Patent
Gilad et al.

(10) Patent No.: US 7,946,979 B2
(45) Date of Patent: May 24, 2011

(54) IMMOBILIZABLE IN VIVO SENSING DEVICE

(75) Inventors: Zvika Gilad, Haifa (IL); Gavriel J. Iddan, Haifa (IL)

(73) Assignee: Given Imaging, Ltd., Yoqneam (IL)

( * ) Notice: Subject to any disclaimer, the term of this patent is extended or adjusted under 35 U.S.C. 154(b) by 890 days.

(21) Appl. No.: 10/540,890

(22) PCT Filed: Dec. 25, 2003

(86) PCT No.: PCT/IL03/01104
§ 371 (c)(1),
(2), (4) Date: Feb. 23, 2006

(87) PCT Pub. No.: WO2004/058041
PCT Pub. Date: Jul. 15, 2004

(65) Prior Publication Data
US 2006/0167339 A1    Jul. 27, 2006

Related U.S. Application Data

(60) Provisional application No. 60/436,003, filed on Dec. 26, 2002.

(51) Int. Cl.
*A61B 1/00* (2006.01)
(52) U.S. Cl. .......................... 600/109; 600/118; 600/106
(58) Field of Classification Search .................. 600/101, 600/104, 106, 109, 114–115, 117–118, 301–302, 600/309, 421, 424, 461, 471, 476, 582
See application file for complete search history.

(56) References Cited

U.S. PATENT DOCUMENTS

| | | |
|---|---|---|
| 3,190,286 A | 6/1965 | Stokes |
| 3,528,429 A | 9/1970 | Beal et al. |
| 3,643,653 A | 2/1972 | Takahashi et al. |
| 3,683,389 A | 8/1972 | Hollis |
| 3,683,890 A | 8/1972 | Beal |
| 3,719,183 A | 3/1973 | Schwartz |
| 3,888,237 A | 6/1975 | Mori |
| 3,971,362 A | 7/1976 | Pope et al. |
| 4,040,413 A | 8/1977 | Ohshiro et al. |
| 4,083,369 A | 4/1978 | Sinnreich |
| 4,148,307 A | 4/1979 | Utsugi et al. |
| 4,176,662 A | 12/1979 | Frazer et al. |
| 4,178,735 A | 12/1979 | Jackson |

(Continued)

FOREIGN PATENT DOCUMENTS

DE    34 40 177    5/1986

(Continued)

OTHER PUBLICATIONS

International Search Report for PCT/IL2003/001104 dated Oct. 1 2004.

(Continued)

*Primary Examiner* — John P Leubecker
*Assistant Examiner* — Samuel Candler
(74) *Attorney, Agent, or Firm* — Pearl Cohen Zedek Latzer, LLP (57) ABSTRACT

An in vivo sensing device including an immobilizer that may immobilize the device in an in vivo location. The immobilizer may be activated by for example a processor or in response to an in vivo condition or in response to a signal from an outside operator.

28 Claims, 6 Drawing Sheets

U.S. PATENT DOCUMENTS

| | | | |
|---|---|---|---|
| 4,217,045 A | 8/1980 | Ziskind | |
| 4,239,040 A | 12/1980 | Hosoya et al. | |
| 4,262,632 A | 4/1981 | Hanton et al. | |
| 4,278,077 A | 7/1981 | Mizumoto | |
| 4,389,208 A | 6/1983 | LeVeen et al. | |
| 4,425,117 A * | 1/1984 | Hugemann et al. | 604/244 |
| 4,439,197 A | 3/1984 | Honda et al. | |
| 4,456,011 A | 6/1984 | Warnecke | |
| 4,646,724 A | 3/1987 | Sato et al. | |
| 4,689,621 A | 8/1987 | Kleinberg | |
| 4,741,327 A | 5/1988 | Yabe | |
| 4,803,992 A | 2/1989 | Lemelson | |
| 4,819,620 A | 4/1989 | Okutsu | |
| 4,844,076 A | 7/1989 | Lesho et al. | |
| 4,878,898 A | 11/1989 | Griffin et al. | |
| 4,915,113 A | 4/1990 | Holman | |
| 4,929,214 A | 5/1990 | Liebermann et al. | |
| 4,936,823 A | 6/1990 | Colvin et al. | |
| 4,940,997 A | 7/1990 | Hamlin et al. | |
| 5,042,486 A | 8/1991 | Pfeiler et al. | |
| 5,081,041 A | 1/1992 | Yafuso et al. | |
| 5,108,407 A * | 4/1992 | Geremia et al. | 606/108 |
| 5,109,870 A | 5/1992 | Silny et al. | |
| 5,187,572 A | 2/1993 | Nakamura et al. | |
| 5,191,879 A | 3/1993 | Krauter | |
| 5,195,955 A | 3/1993 | don Michael et al. | |
| 5,211,165 A | 5/1993 | Dumoulin et al. | |
| 5,267,033 A | 11/1993 | Hoshino | |
| 5,279,607 A | 1/1994 | Schentag et al. | |
| 5,318,589 A | 6/1994 | Lichtman | |
| 5,330,427 A | 7/1994 | Weissenburger | |
| 5,337,732 A | 8/1994 | Grundfest et al. | |
| 5,368,027 A | 11/1994 | Lubbers et al. | |
| 5,395,366 A | 3/1995 | D'Andrea et al. | |
| 5,398,670 A | 3/1995 | Ortiz et al. | |
| 5,421,337 A | 6/1995 | Richards-Kortum et al. | |
| 5,429,132 A | 7/1995 | Guy et al. | |
| 5,479,935 A | 1/1996 | Essen-Moller | |
| 5,495,114 A | 2/1996 | Adair | |
| 5,549,109 A | 8/1996 | Samson et al. | |
| 5,553,741 A | 9/1996 | Sancoff et al. | |
| 5,558,640 A | 9/1996 | Pfeiler et al. | |
| 5,575,754 A | 11/1996 | Konomura | |
| 5,595,565 A | 1/1997 | Treat et al. | |
| 5,604,531 A | 2/1997 | Iddan et al. | |
| 5,697,384 A | 12/1997 | Miyawaki et al. | |
| 5,723,844 A | 3/1998 | Dow et al. | |
| 5,782,771 A * | 7/1998 | Hussman | 600/478 |
| 5,800,350 A | 9/1998 | Coppleson et al. | |
| 5,819,736 A | 10/1998 | Avny et al. | |
| 5,830,217 A | 11/1998 | Ryan et al. | |
| 5,833,603 A | 11/1998 | Kovacs et al. | |
| 5,837,196 A | 11/1998 | Pinkel et al. | |
| 5,853,005 A | 12/1998 | Scanlon | |
| 5,904,647 A | 5/1999 | Ouchi | |
| 5,913,820 A | 6/1999 | Bladen et al. | |
| 5,929,901 A | 7/1999 | Adair et al. | |
| 5,938,585 A | 8/1999 | Donofrio | |
| 5,947,924 A | 9/1999 | Liprie et al. | |
| 5,984,860 A | 11/1999 | Shan et al. | |
| 5,986,693 A | 11/1999 | Adair et al. | |
| 5,993,378 A | 11/1999 | Lemelson | |
| 6,007,482 A | 12/1999 | Madni et al. | |
| 6,010,453 A | 1/2000 | Fiddian-Green | |
| 6,019,721 A | 2/2000 | Holmes et al. | |
| 6,043,839 A | 3/2000 | Adair et al. | |
| 6,074,349 A | 6/2000 | Crowley | |
| 6,099,482 A | 8/2000 | Brune et al. | |
| 6,149,581 A | 11/2000 | Klingenstein | |
| 6,162,171 A | 12/2000 | Ng et al. | |
| 6,165,128 A | 12/2000 | Cespedes et al. | |
| 6,174,291 B1 | 1/2001 | McMahon | |
| 6,228,048 B1 | 5/2001 | Robbins | |
| 6,233,476 B1 | 5/2001 | Strommer et al. | |
| 6,240,312 B1 | 5/2001 | Alfano et al. | |
| 6,251,093 B1 | 6/2001 | Valley et al. | |
| 6,266,550 B1 | 7/2001 | Selmon et al. | |
| 6,285,897 B1 * | 9/2001 | Kilcoyne et al. | 600/350 |
| 6,324,418 B1 | 11/2001 | Crowley et al. | |
| 6,338,709 B1 | 1/2002 | Geoffrion et al. | |
| 6,364,830 B1 | 4/2002 | Durell | |
| 6,369,812 B1 | 4/2002 | Lyriboz et al. | |
| 6,395,562 B1 | 5/2002 | Hammock et al. | |
| 6,402,686 B1 | 6/2002 | Ouchi et al. | |
| 6,458,074 B1 * | 10/2002 | Matsui et al. | 600/106 |
| 6,471,631 B1 | 10/2002 | Slater et al. | |
| 6,475,145 B1 | 11/2002 | Baylor | |
| 6,488,694 B1 | 12/2002 | Lau et al. | |
| 6,527,753 B2 * | 3/2003 | Sekine et al. | 604/264 |
| 6,535,764 B2 * | 3/2003 | Imran et al. | 607/40 |
| 6,549,796 B2 | 4/2003 | Sohrab | |
| 6,579,311 B1 * | 6/2003 | Makower | 623/1.23 |
| 6,612,982 B1 | 9/2003 | Ouchi et al. | |
| 6,632,175 B1 | 10/2003 | Marshall | |
| 6,648,814 B2 * | 11/2003 | Kim et al. | 600/114 |
| 6,689,056 B1 * | 2/2004 | Kilcoyne et al. | 600/300 |
| 6,692,430 B2 | 2/2004 | Adler | |
| 6,692,432 B1 | 2/2004 | Yarush et al. | |
| 6,702,734 B2 | 3/2004 | Kim et al. | |
| 6,709,387 B1 | 3/2004 | Glukhovsky et al. | |
| 6,719,684 B2 | 4/2004 | Kim et al. | |
| 6,776,165 B2 | 8/2004 | Jin et al. | |
| 6,783,499 B2 | 8/2004 | Schwartz et al. | |
| 6,929,636 B1 | 8/2005 | von Alten et al. | |
| 6,934,573 B1 | 8/2005 | Glukhovsky et al. | |
| 6,950,690 B1 | 9/2005 | Meron et al. | |
| 6,951,536 B2 | 10/2005 | Yokoi et al. | |
| 6,979,290 B2 | 12/2005 | Mourlas et al. | |
| 7,009,634 B2 | 3/2006 | Iddan et al. | |
| 7,044,908 B1 | 5/2006 | Montalbo et al. | |
| 7,066,879 B2 | 6/2006 | Fowler et al. | |
| 7,066,880 B2 | 6/2006 | Wendlandt | |
| 7,076,305 B2 * | 7/2006 | Imran et al. | 607/40 |
| 7,107,100 B2 * | 9/2006 | Imran et al. | 607/40 |
| 7,118,529 B2 | 10/2006 | Glukhovsky et al. | |
| 7,122,001 B2 | 10/2006 | Uchiyama et al. | |
| 7,160,258 B2 * | 1/2007 | Imran et al. | 600/593 |
| 7,175,593 B2 | 2/2007 | Durell | |
| 7,261,728 B2 * | 8/2007 | Long et al. | 606/207 |
| 7,509,174 B2 * | 3/2009 | Imran et al. | 607/133 |
| 7,727,169 B1 | 6/2010 | Lewkowicz et al. | |
| 2001/0017649 A1 | 8/2001 | Yaron | |
| 2001/0025135 A1 | 9/2001 | Naito et al. | |
| 2001/0035902 A1 | 11/2001 | Iddan et al. | |
| 2001/0049497 A1* | 12/2001 | Kalloo et al. | 604/164.01 |
| 2001/0051766 A1 | 12/2001 | Gazdzinski | |
| 2002/0015952 A1 | 2/2002 | Anderson et al. | |
| 2002/0042562 A1 | 4/2002 | Meron et al. | |
| 2002/0103417 A1 | 8/2002 | Gazdzinski | |
| 2002/0109774 A1 | 8/2002 | Meron et al. | |
| 2002/0138009 A1* | 9/2002 | Brockway et al. | 600/485 |
| 2002/0146368 A1 | 10/2002 | Meron et al. | |
| 2002/0156347 A1* | 10/2002 | Kim et al. | 600/160 |
| 2002/0158976 A1 | 10/2002 | Vni et al. | |
| 2002/0165589 A1 | 11/2002 | Imran et al. | |
| 2002/0173718 A1 | 11/2002 | Frisch et al. | |
| 2002/0177779 A1 | 11/2002 | Adler et al. | |
| 2002/0198470 A1 | 12/2002 | Imran et al. | |
| 2003/0013370 A1 | 1/2003 | Glukhovsky | |
| 2003/0018280 A1 | 1/2003 | Lewkowicz et al. | |
| 2003/0020810 A1 | 1/2003 | Takizawa et al. | |
| 2003/0023150 A1 | 1/2003 | Yokoi et al. | |
| 2003/0028078 A1 | 2/2003 | Glukhovsky | |
| 2003/0045790 A1 | 3/2003 | Lewkowicz et al. | |
| 2003/0092964 A1 | 5/2003 | Kim et al. | |
| 2003/0114742 A1 | 6/2003 | Lewkowicz et al. | |
| 2003/0117491 A1 | 6/2003 | Avni et al. | |
| 2003/0130562 A1 | 7/2003 | Barbato et al. | |
| 2003/0167000 A1 | 9/2003 | Mullick et al. | |
| 2003/0167024 A1* | 9/2003 | Imran et al. | 601/15 |
| 2003/0171648 A1 | 9/2003 | Yokoi et al. | |
| 2003/0171649 A1 | 9/2003 | Yokoi et al. | |
| 2003/0171652 A1 | 9/2003 | Yokoi et al. | |
| 2003/0195415 A1 | 10/2003 | Iddan | |
| 2003/0208107 A1 | 11/2003 | Refael | |
| 2003/0214579 A1 | 11/2003 | Iddan | |
| 2003/0214580 A1 | 11/2003 | Iddan | |

| | | | |
|---|---|---|---|
| 2003/0216622 | A1 | 11/2003 | Meron et al. |
| 2004/0027459 | A1 | 2/2004 | Segawa et al. |
| 2004/0073087 | A1 | 4/2004 | Glukhovsky et al. |
| 2004/0092825 | A1 | 5/2004 | Madar et al. |
| 2004/0097791 | A1 | 5/2004 | Tokuda et al. |
| 2004/0133076 | A1 | 7/2004 | Kobayashi et al. |
| 2004/0153008 | A1* | 8/2004 | Sharf et al. ............... 600/588 |
| 2004/0176664 | A1 | 9/2004 | Iddan |
| 2004/0186349 | A1 | 9/2004 | Ewers et al. |
| 2004/0225189 | A1 | 11/2004 | Kimoto et al. |
| 2005/0143624 | A1 | 6/2005 | Iddan |
| 2006/0004255 | A1 | 1/2006 | Iddan et al. |
| 2007/0270651 | A1 | 11/2007 | Gilad et al. |

FOREIGN PATENT DOCUMENTS

| | | |
|---|---|---|
| DE | 1002853 | 12/2000 |
| FR | 2 688 997 | 10/1993 |
| IL | 126727 | 10/1998 |
| IL | 143258 | 5/2001 |
| IL | 143259 | 5/2001 |
| JP | 57045833 | 3/1982 |
| JP | 68-019233 | 2/1983 |
| JP | 3-289779 | 12/1991 |
| JP | 4109927 | 4/1992 |
| JP | 1992-144533 | 5/1992 |
| JP | 4-180736 | 6/1992 |
| JP | 04-347138 | 12/1992 |
| JP | 5015515 | 1/1993 |
| JP | 06-063030 | 3/1994 |
| JP | 06-114036 | 4/1994 |
| JP | 06114036 A * | 4/1994 |
| JP | 06-142081 | 5/1994 |
| JP | 6142081 | 5/1994 |
| JP | 06-285044 | 10/1994 |
| JP | 07-111-985 | 5/1995 |
| JP | 7289504 | 11/1995 |
| JP | 09327447 A | 12/1997 |
| JP | 2000-342522 | 12/2000 |
| JP | 2000-342524 | 12/2000 |
| JP | 2000-342525 | 12/2000 |
| JP | 2001-091860 | 4/2001 |
| JP | 2001-095755 | 4/2001 |
| JP | 2001-095756 | 4/2001 |
| JP | 2001-104241 | 4/2001 |
| JP | 2001-104242 | 4/2001 |
| JP | 2001-104243 | 4/2001 |
| JP | 2001-104244 | 4/2001 |
| JP | 2001-104287 | 4/2001 |
| JP | 2001-112709 | 4/2001 |
| JP | 2001-112710 | 4/2001 |
| JP | 2001-112740 | 4/2001 |
| JP | 2001-137182 | 5/2001 |
| JP | 2001-224551 | 8/2001 |
| JP | 2001-231744 | 8/2001 |
| JP | 2001224553 | 8/2001 |
| JP | 2001-245844 | 9/2001 |
| JP | 2001-297703 | 9/2001 |
| JP | 2002-010990 | 1/2002 |
| JP | 04-176443 | 6/2006 |
| WO | WO 92/21307 | 12/1992 |
| WO | WO 98/11816 | 3/1998 |
| WO | WO 99/32028 | 7/1999 |
| WO | WO 01/08548 | 2/2001 |
| WO | WO 01/10291 | 2/2001 |
| WO | WO 01/53792 | 6/2001 |
| WO | WO 01/50941 | 7/2001 |
| WO | WO 01/65995 | 9/2001 |
| WO | WO 2001/69212 | 9/2001 |
| WO | WO 01/87377 | 11/2001 |
| WO | WO 02/26103 | 4/2002 |
| WO | WO 02/55984 | 7/2002 |
| WO | WO 02/67593 | 8/2002 |
| WO | WO 02/094337 | 11/2002 |
| WO | WO 2003/003706 | 1/2003 |
| WO | WO 2003/011103 | 2/2003 |
| WO | WO 03/090618 | 11/2003 |
| WO | WO 2004/028336 | 4/2004 |
| WO | WO 2004/035106 | 4/2004 |
| WO | WO 2004/058041 | 7/2004 |

OTHER PUBLICATIONS

Rowlands, et al.: "The Radio Pill", British Communications and Electronics, Aug. 1960, pp. 598-601.
"Video Camera to Take"—RF Systems Lab.
Crum: "Wellesley company sends body monitors into space", Apr. 1998.
Swain, CP., Gong, F. Mills TN.: "Wireless transmission of a color television moving image from the stomach using a miniature CCD camera, light source and microwave transmitter", Gastrointest Endosc 1997;45:AB40.
PCT International Search Report of International Application No. PCT/IL01/00912.
BBC News Online—Pill camera to 'broadcast from the gut', Feb. 21, 2000, www.news.bbc.co.uk.
Office Action for U.S. Appl. No. 09/963,950 mailed Sep. 29, 2003.
Office Action for U.S. Appl. No. 09/963,950 mailed Apr. 8, 2004.
Office Action for U.S. Appl. No. 09/963,950 mailed Jan. 26. 2005.
Office Action in U.S. Appl. No. 09/963,950 dated Apr. 8, 2004.
Office Action in U.S. Appl. No. 09/963,950 dated Sep. 29, 2003.
Office Action in U.S. Appl. No. 09/963,950 dated Jan. 26, 2005.
Office Action issued in U.S. Appl. No. 11/025,124 dated Feb. 20, 2009.
Office Action issued in U.S. Appl. No. 11/025,124 dated Aug. 28, 2009.
Office Action of U.S. Appl. No. 11/025,124, dated Feb. 1, 2010.
Office Action of U.S. Appl. No. 11/802,121, dated Dec. 1, 2009.
English translation of Japanese Office Action, issued Feb. 16, 2010, in connection with Japanese Patent Application No. 2004-563550.
U.S. Appl. No. 12/700,596, filed Feb. 4, 2010, Lewkowicz, S. et al.
Office Action, issued Nov. 25, 2005, for U.S. Appl. No. 10/423,023.
Final Office Action, issued Jul. 12, 2006, for U.S. Appl. No. 10/423,023.
Office Action, issued Mar. 29, 2007, for U.S. Appl. No. 10/423,023.
Final Office Action, issued Dec. 11, 2007, for U.S. Appl. No. 10/423,023.
Office Action, issued Dec. 31, 2008, for U.S. Appl. No. 10/423,023.
Final Office Action, issued Aug. 4, 2009, for U.S. Appl. No. 10/423,023.
Final Office Action, issued May 24, 2010, for U.S. Appl. No. 11/802,121.
Final Office Action, issued Jul. 21, 2010, for U.S. Appl. No. 11/025,124.
U.S. Appl. No. 09/800,470, filed Mar. 8, 2001, Iddan et al.
U.S. Appl. No. 10/213,345, filed Aug. 7, 2002, Glukhovsky.
U.S. Appl. No. 60/297,761, filed Jun. 14, 2001, Lewkowicz et al.
Mackay, R.S. et al., "Bio-Medical Telemetry: Sensing and Transmitting Biological Information from Animals and Man," John Wiley and Sons, New York, 1970, pp. 244-245.
Yarbrough III, D.R. et al., "Evaluation of the Heidelberg pH Capsule: Method of Tubeless Gastric Analysis," The American Journal of Surgery, vol. 117, Feb. 1969, pp. 185-192.
Craford, M.G. et al., "In Pursuit of the Ultimate Lamp," Scientific America, Feb. 2001, pp. 49-53.
Katgraber F. et al., "Mechanism of fatal air embolism after gastrointestinal endoscopy," International Journal of Legal Medicine, vol. 111(3), 1998, pp. 154-156.
Thompson, M.M. et al. (Eds), "Manual of Photogrammetry, 3rd Edition, vol. II" Copyright 1944, 1952, 1966 by the American Society of Photogrammetry.
Turke, Z. "New Smart Plastic has Good Memory," European Medical Device Manufacturer, devicelink.com, Jun. 2, 2001.
Shin-ichi, T. et al., "Robots for the Future," printed from http://jin.jcic.or.jp/nipponaia13/sp05.html on Nov. 29, 2001.
"The Heidelburg pH Capsule System Telemetric Fasting Gastric Analysis," Heidelburg International, Incorporated.
Wang, L. et al., "Intergrated Micro-Instrumentation for Dynamic Monitoring of the Gastro-Intestinal Tract," Presented at the IEEE Instrumentation and Measurement Technology Conference, May 2002, Anchorage, AK; www.see.ed.ac.uk/Naa.publications.html.

"Tiny Cam" printed from www.jason.net/tinycam.htm on Dec. 19, 2001; Copyright 2000 by Jason Chan of Hong Kong.

"Review proves the value of computers," printed from www.middleeasthealthmag.com/article2.htm on Nov. 29, 2001; Copyright 2001.

Pages printed from Personal Electronic Devices, Inc., http://www.pedinc.com/; Copyright 1997.

"Norika 3," pp. printed from www.rfnorika.com on Jan. 1, 2002, Copyright 2001 RF SYSTEMlab.

Office Action, issued Oct. 28, 2010, for U.S. Appl. No. 11/025,124.

Office Action, issued Feb. 8, 2011, for U.S. Appl. No. 11/025,124.

* cited by examiner

IMMOBILIZABLE IN VIVO SENSING DEVICE

CROSS-REFERENCE TO RELATED APPLICATIONS

This application is a National Phase Application of PCT International Application No. PCT/IL2003/001104, International Filing Date Dec. 25, 2003, claiming priority of U.S. Provisional Patent Application 60/436,003, filed Dec. 26, 2002, both of which are incorporated by reference herein in their entirety.

FIELD OF THE INVENTION

The present invention relates to in vivo sensing devices generally and to their immobilization in vivo, in particular

BACKGROUND OF THE INVENTION

In vivo sensing devices, such as thermometers, pH meters, optical scanners, image sensors and so on, may be used for example to unobtrusively monitor bodily systems and in vivo sites. Some in vivo sensors move through body lumens and may be remotely controlled. However, it may sometimes be desirable to immobilize a sensing device in vivo for continuous sensing of an in vivo site, for example, for post surgery monitoring. Other in vivo sensors may perform treatment functions and may be immobilized to perform such treatment. Still other in vivo sensors may be immobilized to monitor an area for a period of time in order to make a diagnosis, such as an in vivo pH sensor which may be immobilized to detect, record and analyze gastroesophageal pH. Immobilization of a device may also provide an opportunity for the device to release a compound such as a drug at a specific location or for taking a biopsy at such location.

SUMMARY OF THE INVENTION

In embodiments of the invention an in vivo sensing device may include an immobilizer or immobilization unit that may be activated in response to a signal from for example a processor or controller. According to one embodiment, the immobilizer may immobilize the device in an in vivo area that is to be monitored over a period of time. In some embodiments, the in vivo sensing device may be or include an autonomous in vivo sensing capsule. In accordance with embodiments of a method of the invention a signal may be generated to activate an immobilizer that is included in an in vivo device so that the in vivo device is immobilized in an in vivo area to be monitored. The immobilized in vivo device may continue to monitor or collect images or other sensing data from the area that is proximate to the device.

In accordance with a system of the invention, a housing may include or be attached to an in vivo sensor and an immobilizing unit, and may also include a processor that may activate the immobilization unit.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 3 is a schematic flow chart diagram presentation of a method in accordance with certain embodiments of the present invention It will be appreciated that for simplicity and clarity of illustration, elements shown in the figures have not necessarily been drawn to scale For example, the dimensions of some of the elements may be exaggerated relative to other elements for purposes of clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However; it will be understood by those skilled in the art that the present invention may be practiced without these specific details. In other instances, well-known methods, procedures, and components have not been described in detail so as not to obscure the present invention.

According to an embodiment of the present invention there is provided a device, system and method for immobilizing or otherwise controlling the movement of or holding a sensing device in an in vivo site for example in response to a signal that activates an immobilization unit or in response to another condition or event such as for example the passage of time Some embodiments may enable for example a doctor or other operator to indicate to an in vivo device such as for example an autonomous in vivo capsule, to stop the movement of the device in vivo or to direct that the device assume an immobilized state or position. Immobilizing an in vivo device may be desirable for example, if something of concern, such as blood, a high temperature, a polyp or other protrusion, is detected while the sensor moves for example through a body lumen, and the operator wants to monitor the item of concern or particular in vivo site more carefully or for a longer period of time. In some embodiments, monitoring may include for example capturing images of the in vivo site or performing other sensing functions in the area proximate to where the device is immobilized. In some embodiments, a sensing device may be stopped or held at one or more known locations in the body lumen to recalibrate sensors in the device to those locations.

According to one embodiment, a device of the invention may include a sensing device, a transmitter that transmits the output of the sensing device, a reception system for receiving the transmitted output and a power source, which provides power to the elements of the device. The sensing device may be connected to, or disposed within, a housing or shell, which may be configured for being transiently immobilized or held proximate to or in the vicinity of the site to be monitored. According to other embodiments, the device may be permanently immobilized in vivo.

The sensing device may be a sensor that is adapted for being placed in vivo, for example, along the gastro-intestinal (GI) tract, and that is configured for sensing in vivo environmental conditions such as for example the presence of blood, pH, temperature, electrical impedance of tissues etc. The sensing device may transmit (such as for example by radio waves) output relating to for example changes in in vivo environmental conditions. Other sensors may be used and other conditions may be detected or monitored.

In some embodiments, a system is provided for monitoring, such as for example by way of an imager, a site in the GI tract over an extended period of time. The imaging system may include at least one illumination source such as one or more light emitting diodes (LED), which may be for example monochromatic or a white LED, and an imaging device such as for example a charge coupled device (CCD) or complementary metal oxide semiconductor (CMOS) image sensor. Other light sources and other suitable imaging devices may be used. The imaging system may further include an optical system for imaging an area of interest onto the imaging system. The optical system may include mirrors and/or lenses for collimating the light from the illumination source. In some embodiments of the invention, a reception system receives the transmitted image output. Such reception system may include an antenna array capable of surrounding a body for receiving the transmitted image output and for producing a plurality of received signals and a demodulator capable of transforming the plurality of received image signals into a single video data stream. The reception system may include for example a display, such as for example an LCD or a monitor, for displaying the data transmitted to it.

Embodiments of the invention may be included in an autonomous device such as for example a self-contained in-vivo capsule capable of passing through a body lumen such as for example a GI tract, the reproductive that, the urinary tract or a blood vessel, and where some or all of the operative components are substantially contained within a container, and where the device does not require wires or cables to for example receive power or transmit information. For example, power may be supplied by an internal battery or wireless receiving system. Other embodiments may have other configurations and capabilities. For example, components may be distributed over multiple sites or units. Control information may be received from an external source.

A device or system in accordance with an embodiment of the invention may include an imager such as for example a camera system, a transmitter, a receiving system and a display system such as described in some embodiments of U.S. Pat. No. 5,604,531 to Iddan and/or in International Application publication number WO 01/65995 entitled "A Device And System For In Vivo Imaging", published on 13 Sep. 2001 U.S. Pat. No. 5,604,531 and WO 01/65995 are assigned to the common assignee of the present invention and are hereby incorporated herein by reference.

An imaging system in accordance with an embodiment of the invention may for example provide direct visual information of an in vivo site such that visibly detectable changes at the site, such as bleeding, swelling etc can be seen by an operator. In some embodiments, the imaging system may further include a detector coupled to the sensor or imaging device that is optically changed in response to changes in environmental conditions. The optical change in the detector may be imaged and transmitted to a receiving system and shown on a display of the receiving unit to alert an external operator of the changed conditions. For example, the imaging system may include a pH meter that undergoes a color change in response to pH changes in its vicinity. In some embodiments, the imaging system may include a detector of chemical substances, such as blood components, which may undergo a change in color in response to the presence of the chemical substances. In both cases, a change in color may be detected by for example an imaging device or other sensor and an indication of such detection may be transmitted and received by the reception system for inspection by for example an operator. In some embodiments, a processor in an external receiving system may analyze a detected condition a may issue signals or instructions in response to said detected conditions. In some embodiments, a sensor such as an imager may signal a processor in the in vivo device as to the presence of a detected condition. In response, a processor or controller may generate a signal that may activate an immobilization unit that may be included in or attached to the device. As described herein, such signal may result in the immobilization of the device in a specific location where further sensing of in vivo conditions may be desired.

Figure 1A:
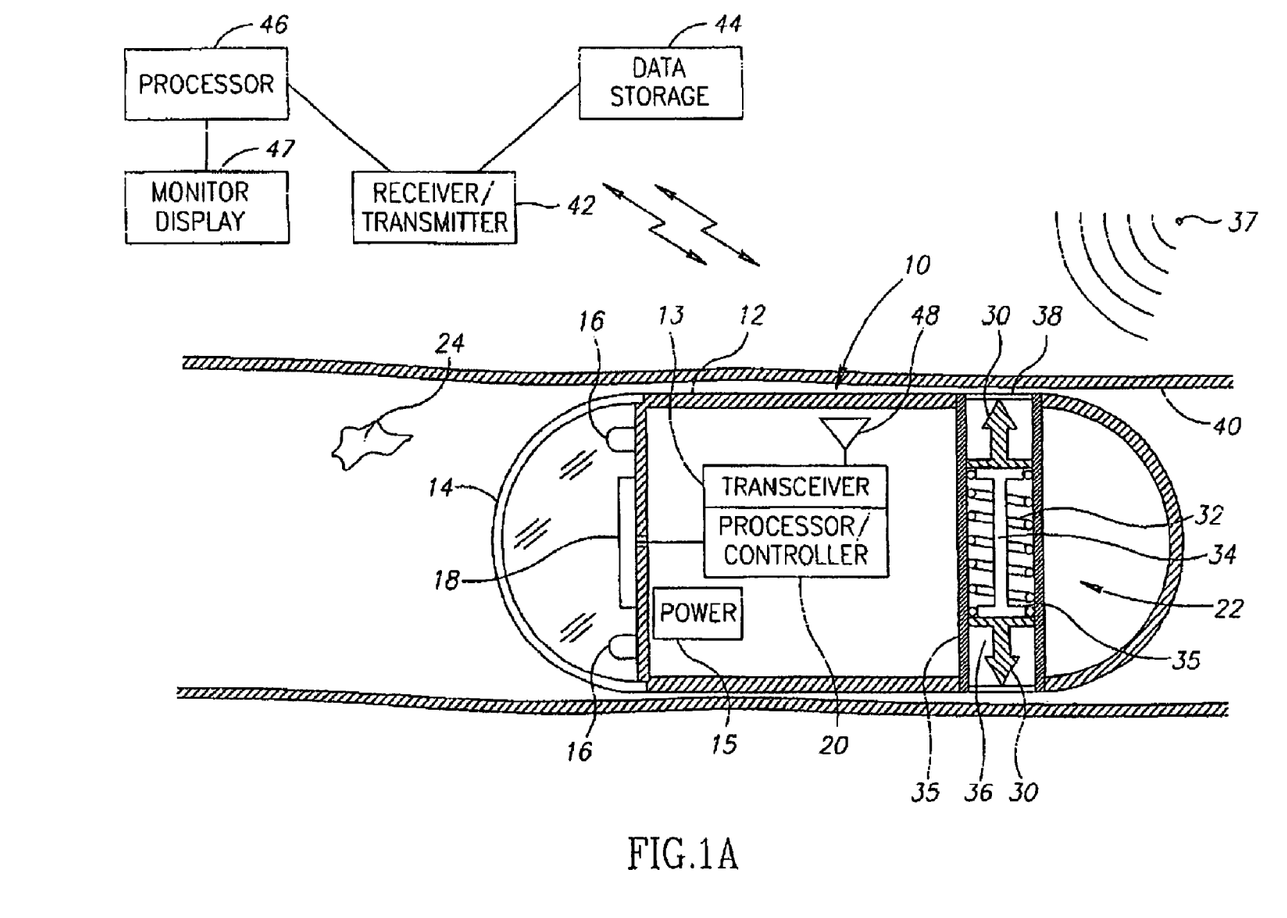
FIG. 1A is a schematic illustration of an in vivo device having an immobilization unit, constructed and operative in accordance with an embodiment of the present invention.
Figure 1B:
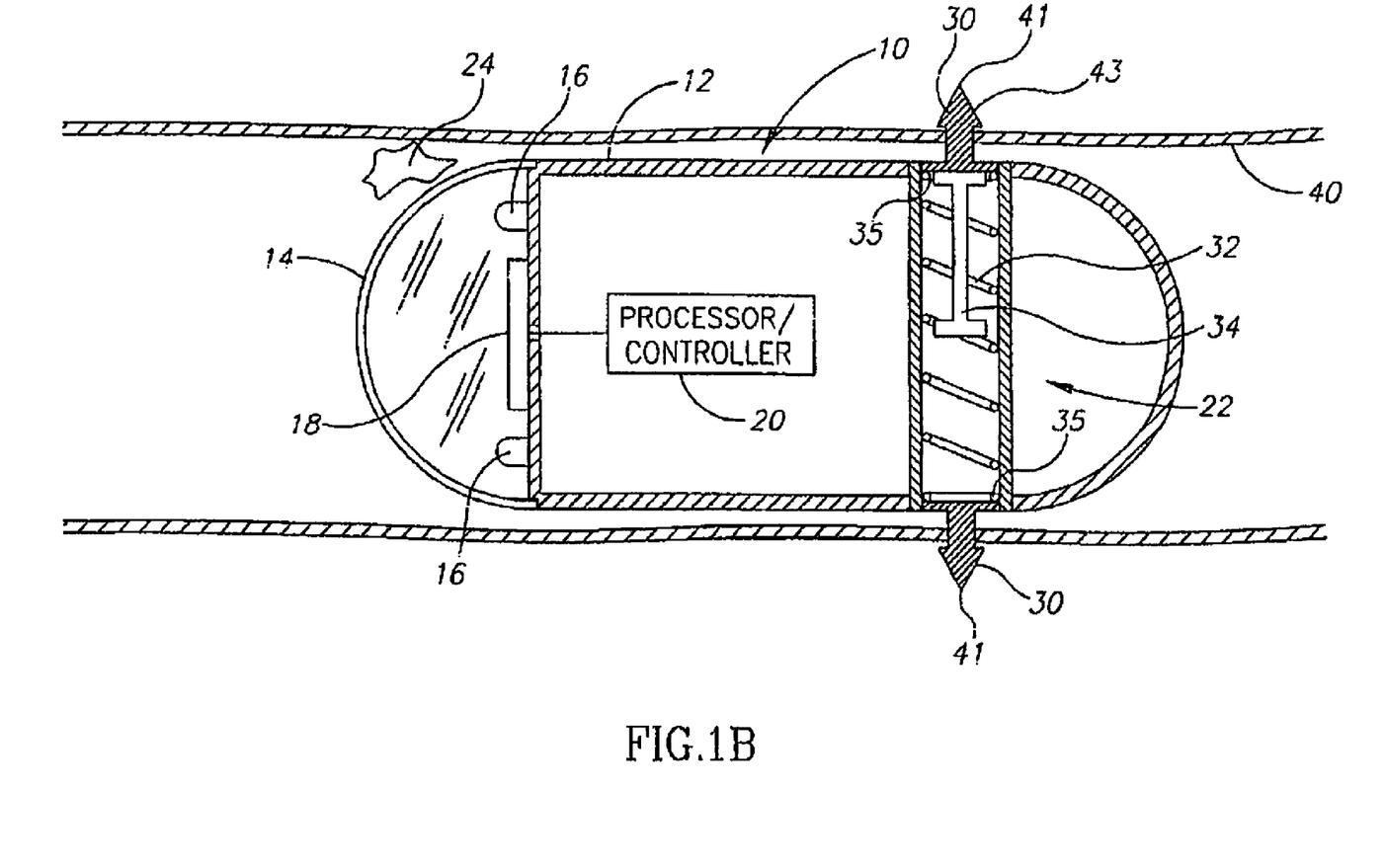
FIG. 1B is a schematic illustration of the in vivo device of FIG. 1A in an immobilized state, in accordance with an embodiment of the present invention.
Figure 1C:
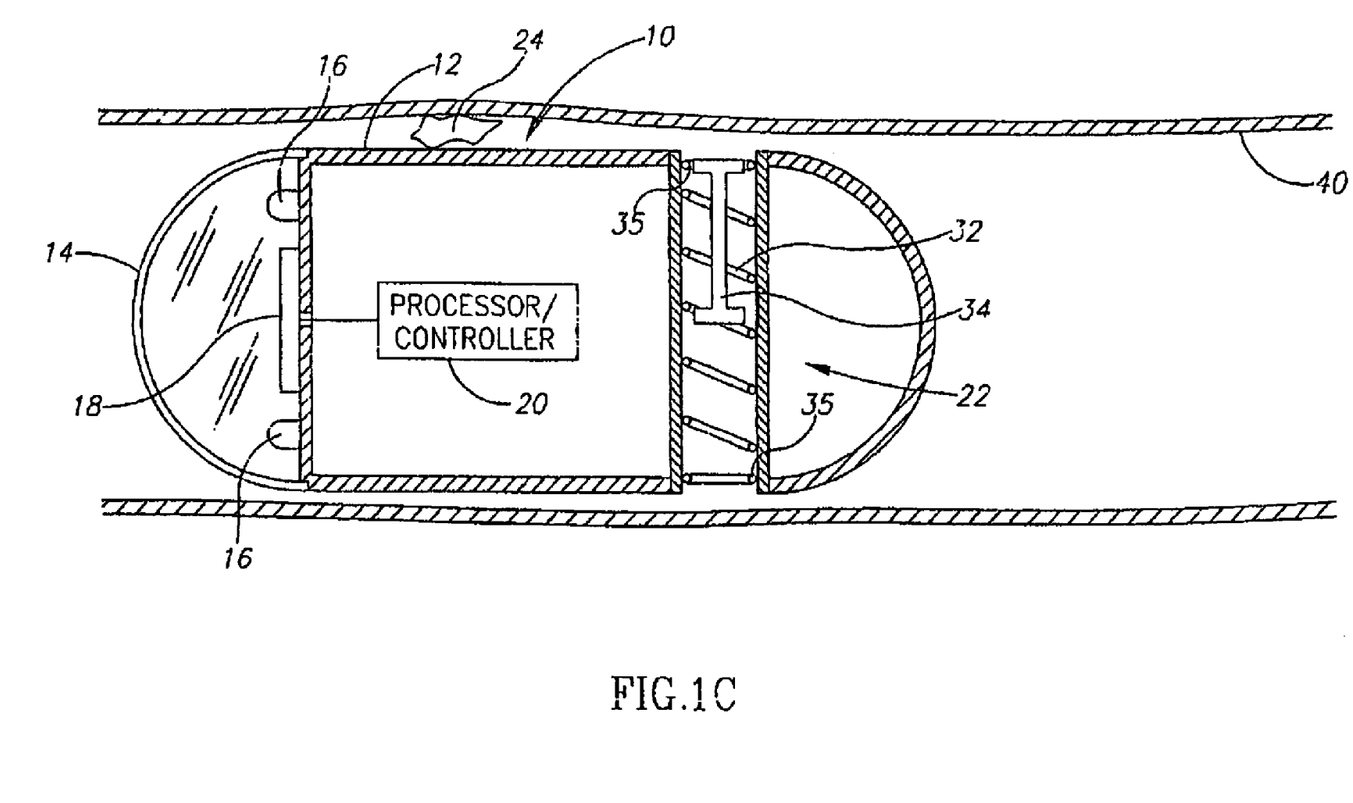
FIG. 1C is a schematic illustration of the in vivo device of FIG. 1A fined from an immobilized state, in accordance with an embodiment of the present invention.

Reference is now made to FIGS. 1A, 1B and 1C which illustrate an in vivo device 10, designed, according to one embodiment, to passively traverse the GI tract. Device 10 may include a housing or body 12, which may include for example an optical window 14, behind or adjacent to which may be positioned illumination sources 16, an imaging device 18, and a controller or processor 20. According to an embodiment of the invention, the body 12 may house additional elements of the system, such as a transceiver 13 for receiving instructions or commands from an external operator or processor and/or for transmitting data such as sensing data to an external receiver/transmitter 42, and a power source 15, such as a battery Transceiver 13 may include one or more antennas 48 or arrays of antennas 48

A system in accordance with some embodiments of the invention may include outside a patient's body a receiver/transmitter 42, which may include an antenna or antenna array, a data storage unit 44, a processor 46 and a display system or monitor 47. Receiver/transmitter 42 may receive signals in the form of for example radio waves that may be transmitted from device 10 and that may for example contain image data, location data and or other sensing data collected by or about device 10. A transmitter such as for example receiver/transmitter 42 may also transmit signals or instructions to device 10 such as for example instructions to immobilize device 10 in a body lumen or to change a state of activation of a component of device 10.

Monitor 47 may include for example one or more screens, monitors or suitable display units. Monitor 47 may for example display images or other data captured or transmitted by device 10. In some embodiments, images and position or location information of such device 10 may be displayed on one or more monitors 47.

In some embodiments, processor 20 may be or include for example one or more circuits such as for example an integrated circuit or circuit board suitable for processing, transmitting or delivering signals from for example a sensing device such as an in vivo imager or from an external transmitter, and for transmitting a signal to an immobilization unit 22. In some embodiments, controller or processor 20 may be or include an electronic, electrical, physical or mechanical controller such as for example a conductive element that may control directly or indirectly the operation of immobilization unit 22. Other controllers or processors 20 may be used.

Device 10 may include an immobilizer or an immobilization unit 22 or other suitable holding system. According to some embodiments, immobilization unit 22 may immobilize, hold or otherwise arrest the motion of the device 10 in response to instructions or signals of processor 20. In some embodiments, an instruction may be or include an electronic or electrical signal such as for example a signal to activate a hearing element. In some embodiments an instruction may include a physical signal such as the opening of latch to release an anchor 30 from a body 12.

In some embodiments the device 10 may be immobilized or held temporarily or transiently such that its movement may resume after a period of time or in response to certain conditions or triggers. In accordance with an embodiment of the present invention, instructions to immobilize device 10 in an in vivo site may come from an external operator, when for example the operator sees or receives an indication of a condition, such as for example a protrusion 24 from an endo-luminal wall, that s/he might want to view for more than the few seconds or minutes typically available during the device's 10 regular traverse of the current region. In some embodiments, instructions or signals to immobilize may be issued by processor 20, or by an external operator for example providing input to a processor 20, in response to an analysis of sensed data that may indicate that there is a condition that may be of concern, such as for example blood in a region of the GI tract. Upon detection of such a condition, processor 20 may instruct or signal immobilization unit 22 to activate, stopping the progress of device 10 through a body lumen.

In the example of FIGS. 1A-1C, immobilizer or immobilization unit 22 may include a set of anchors 30 such as pointed anchors, a spring 32 between anchors 30 and a fuse 34. Other number of anchors 30 such as one anchor may be used. Anchors 30 may have other configurations such as for example a wheel or sphere with talons, points, hooks or other shapes that may be brought into contact with an endo-luminal tissue to immobilize device 10. According to an embodiment of the invention, immobilizer or immobilization unit 22 may be covered, retracted or located within a chamber 36 formed within body 12 and generally sealed from the other chambers of body 12 and from contact with a body lumen until activated. In some embodiments, chamber 36 may have holes to the outside through which anchors 30 may move. In some embodiments, the holes may be covered with a film cover 38 that anchors 30 may break or puncture as they move or are activated.

Spring 32 may be formed of any suitable spring-like material whose ends may be soldered or otherwise releaseably attached to the ends of fuse 34 with soldering or other adhesive material 35, as is depicted in FIG. 1A. Fuse 34 may be formed of a material, such as for example ferrite, which heats up in the presence of a radio frequency. Such a fuse is discussed for example in U.S. Pat. No. 5,723,844 to Dow filed on Mar. 3, 1998 and entitled "Heating System using Ferrite to Convert RF Energy to Heat Energy", which is incorporated herein by reference. Other releasable adhesives or materials may be used to hold spring 32 and other means of releasing spring 32, such as for example with an electrical charge applied to spring 32 or to adhesive material 35, may be used.

In one embodiment, fuse 34 may be activated in response to a signal from for example receiver/transmitter 42, that may be received for example by transceiver 13, and processed by processor 20. In another embodiment, an external transmitter 37 may for example transmit radio waves of the frequency or frequencies which may heat up fuse 34. In such example, when fuse 34 heats up, fuse 34 may break material 35, thereby releasing spring 32 from its contracted state as is depicted in FIG. 1A, and pushing anchors 30 into walls 40 of the GI tract as is shown in FIG. 1B. FIG. 1B shows device 10 stopped at a distance from protrusion 24 such that protrusion 24 might be viewed or sensed in more detail. In some embodiments, transmitter 37 may be included in or connected to receiver/transmitter 42.

An anchor 30 may have a pointed head 41 capable of piercing endo-luminal walls 40. In some embodiments, spring 32 may force head 41 most or all of the way into walls 40. Pointed head 41 may be configured to a suitable size and shape which may hold device 10 in place. For example, head 41 may have a diameter at its point of 0.5-2 mm which may in some embodiments be suitable for immobilizing a device with dimensions of approximately 11 mm by 25 mm. Other suitable dimensions may be used Anchors 30 may be formed of any suitable material such as for example a biodegradable material 43 strong enough to hold device 10 in place but which may degrade or be soluble upon exposure to for example the moist conditions of an in vivo environment such as the GI tract. Suitable materials may include, for example, caramel, biodegradable plastic resins or starches, such as gelatin, or wax. After a period of time, at least biodegradable material 43 of head 41 may dissolve, thereby releasing device 10, and device 10 may continue moving through a body lumen. The latter phase is shown in FIG. 1C where spring 32 is in an expanded state but where anchors 30 have degraded. In FIG. 1C, device 10 is depicted as passing protrusion 24

In accordance with an embodiment of the present invention, the biodegradable material 43 of anchors 30 may include a pharmacological compound or composition. For example, the compound or composition might be or include an antibiotic, for example to counter possible injury caused by anchors 30 when pushed into walls 40

In accordance with an alternative embodiment of the present invention, the compound might be a drug needed at a specific location. In such embodiment, the location, of device 10 as proximate to protrusion 24, may be known and processor 20 may instruct or signal for example fuse 34 or some other mechanism to activate immobilization unit 22 at the appropriate moment to cause anchors 30 to jab walls 40 at the desired location in this embodiment, immobilization unit 22 may act as a drug delivery unit.

According to further embodiments, the biodegradable material 43 of anchors 30 may include in it a marker or any other compound needed to be delivered, preferably in a site-specific manner, to a body lumen, such as the GI tract.

Figure 2A:
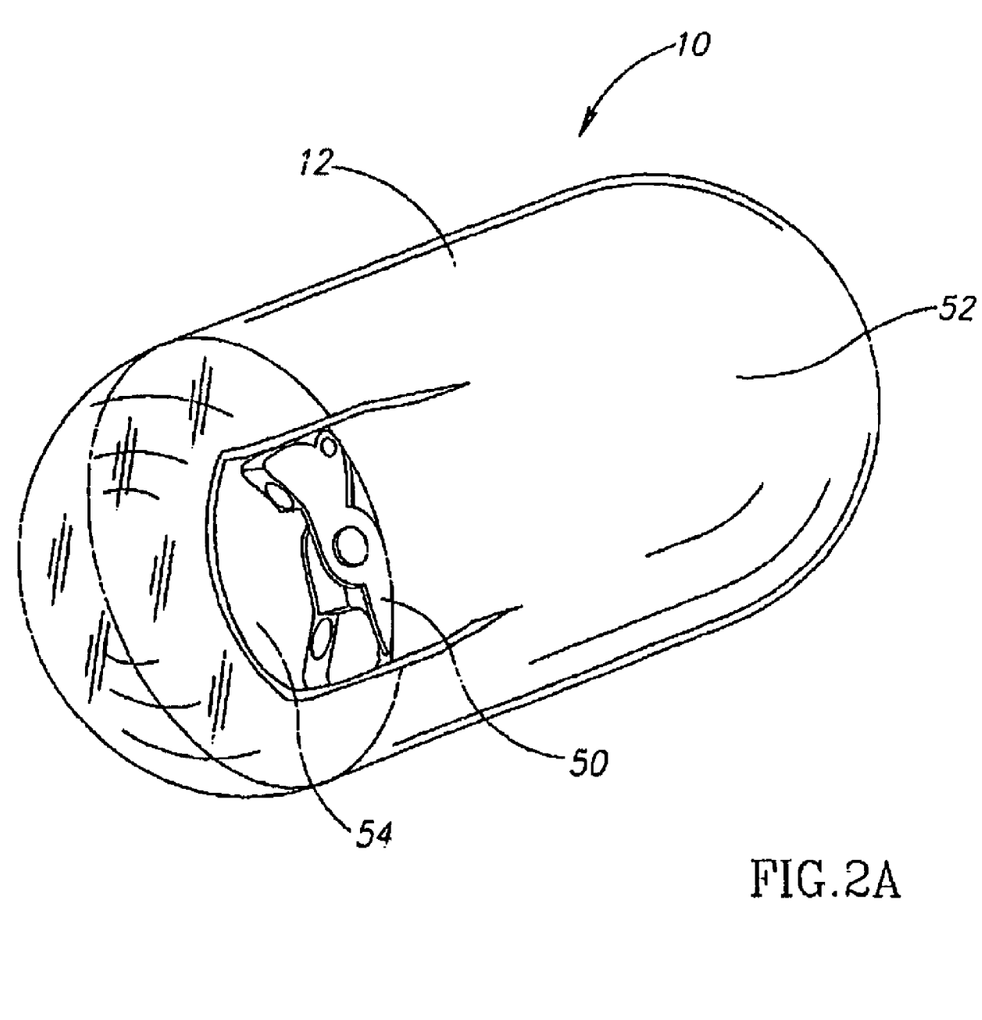
FIG. 2A is a schematic illustration of an in vivo device with a gripping unit, constructed and operative in accordance with an embodiment of the present invention.
Figure 2B:
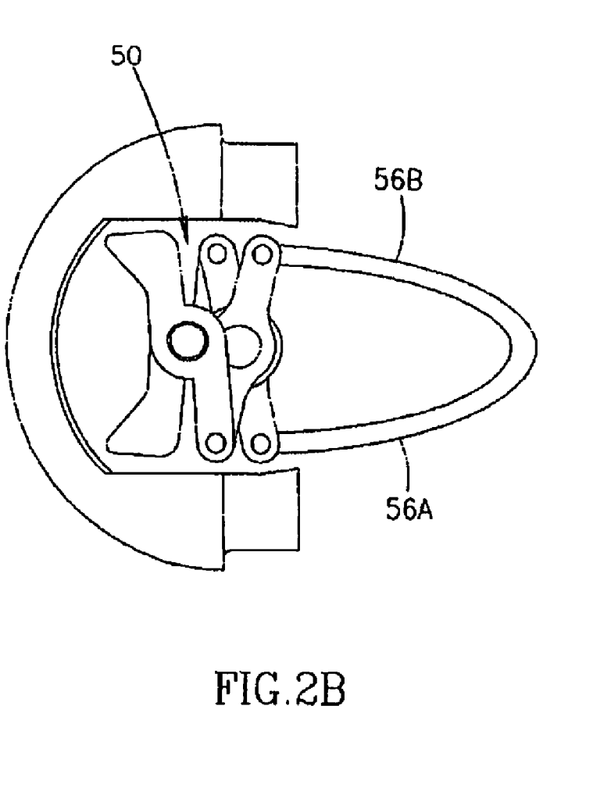
FIG. 2B is a cross-sectional illustration of the gripping unit of FIG. 2A, in accordance with an embodiment of the present invention.
Figure 2C:
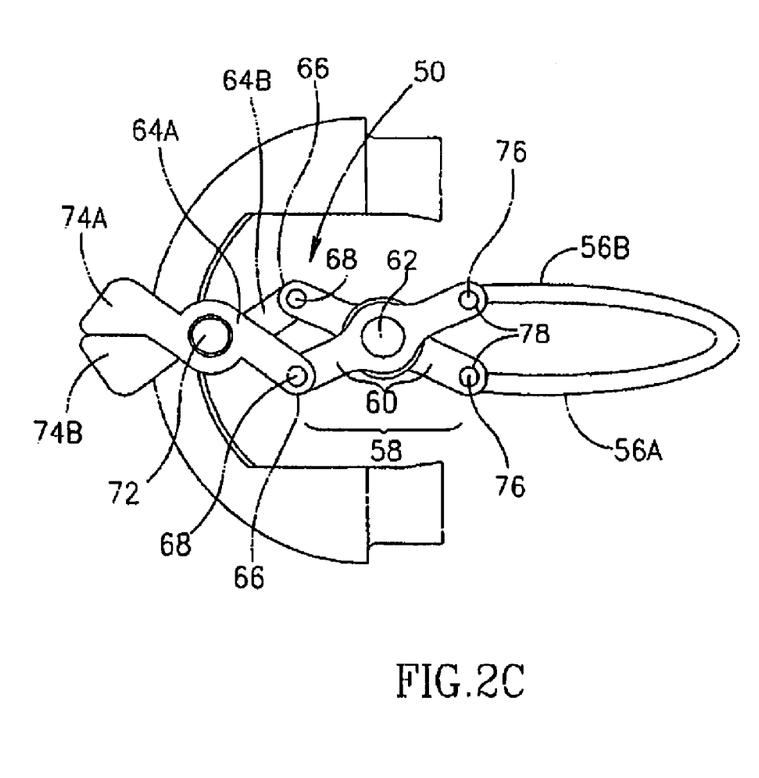
FIG. 2C is a cross-sectional illustration of the gripping unit of FIG. 2A in an extended state, in accordance with an embodiment of the present invention.

Reference is now made to FIGS. 2A, 2B and 2C which illustrate an alternative embodiment of the present invention. In such embodiment, anchors 30 may be replaced by one or more sets of grippers 50, which may extend for example longitudinally along a side 52 of body 12. As in the previous embodiment, grippers 50 may be located within a chamber 54 which may be external to the main chamber of device 10.

As can be seen in FIG. 2B, grippers 50 may be connected to an actuator 56A and 56B, that may be formed for example of a piezoelectric material, such as for example poly vinylidene fluoride (PVDF), commercially available from PIEZOTECH S A. of St. Louis, France. Other activating processes may be used to move, close or open grippers 50, and other materials may be used. When instructed by processor 20 (not shown in FIGS. 2A-C), actuators 56 may change shape or otherwise pull on grippers 50, causing grippers 50 to extend outside of chamber 54 (see FIG. 2C) and, if walls 40 are close by, to grasp or pinch a portion of an endo-luminal wall 40 (not shown). In the latter state, grippers 50 may arrest the motion of device 10. Other mechanisms or processes of activating grippers 50 may be used.

Grippers 50 may be formed of a metal, plastic or other material suitable for use in a body lumen and may be formed of for example a plurality of double scissors mechanisms 58 with rods 60 rotatably joined by a pivot 62 and a gripping end 64. Other configurations for grippers 50 are possible. FIGS. 2B and 2C show, for example, a double scissors mechanism 58, though other closing mechanisms to engage grippers 50 may be utilized. Ends 66 of rods 60 may be rotatably connected, via pivots 68, to ends 70 of gripping end 64. Gripping end 64 may be formed of two halves 64A and 64B, rotatably connected via pivot 72 and ending in opposing gripping shapes 74A and 74B.

Actuators 56 may be formed in a tweezers shape having two pinching halves 56A and 56B, each rotatably connected, via pivots 76, to ends 78 of crossed rod 60. When actuator 56 may be in the open state (FIG. 2B), rods 60 and gripping end 64 may be in their open state and gripping shapes 74A and 74B may remain within chamber 54. However, when actuators 56 may be in a closed state (FIG. 2B), rods 60 and gripping end 64 may extend into their closed states and gripping shapes 74A and 74B may extend outside of chamber 54 in an attempt to pinch walls 40

When desired, and in response to for example a signal or instructions from a processor 20 or an operator, after a predetermined period of time, or after an expected action has occurred or condition has been sensed, processor 20 may provide instructions to actuators 56 to open, thereby retracting grippers 50, freeing device 10 from the in vivo site to which it was immobilized, and enabling device 10 to continue its traverse of a body lumen In some embodiments, such instructions may be provided for example in response to a signal from receiver/transmitter 42 to transceiver 13.

According to another embodiment of the invention grippers 50 may be used to pinch off a piece of tissue, such as while taking a biopsy. While grippers 50 are retracting, the piece of tissue may be collected into a sample container (not shown) that is placed within chamber 54.

Figure 3:
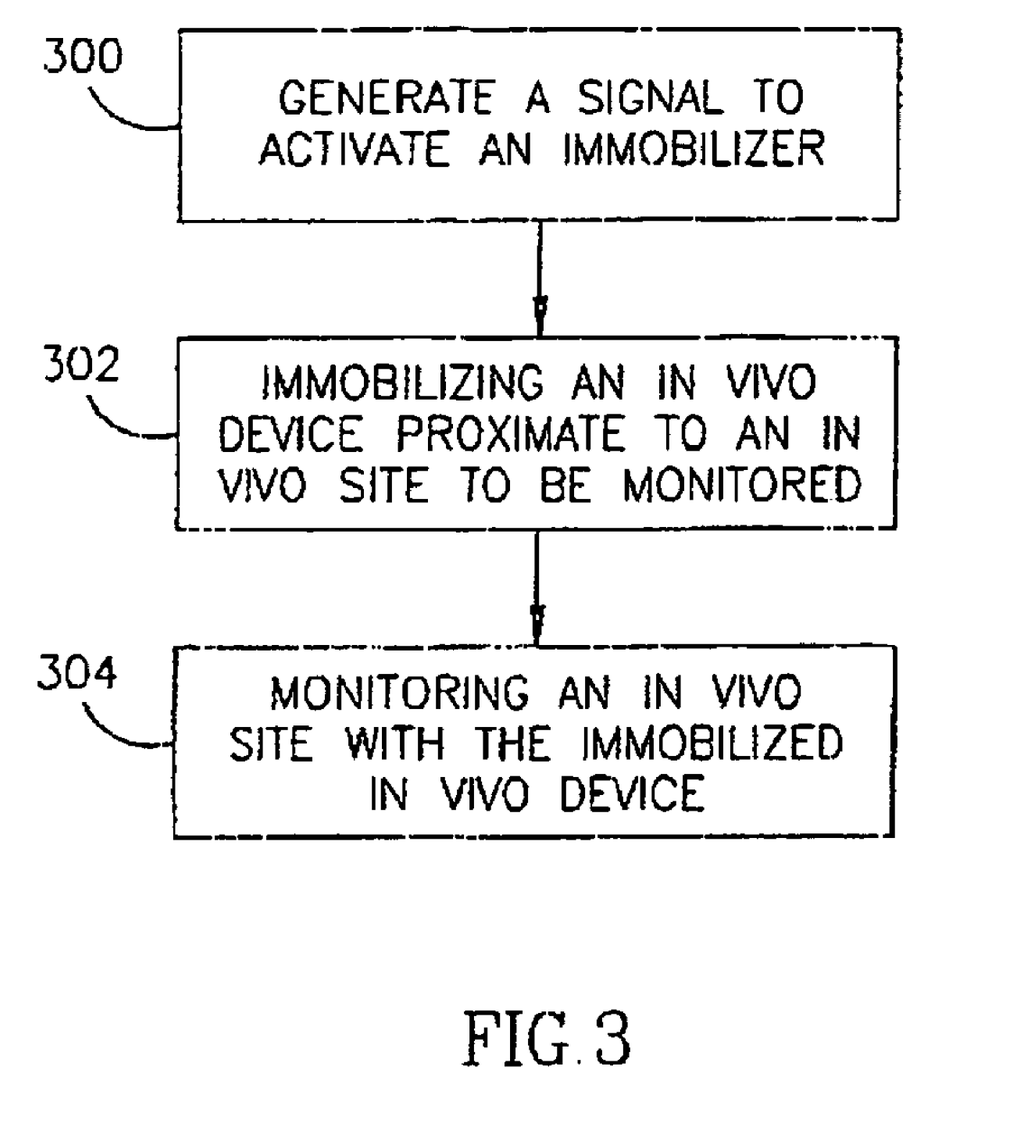

Reference is made to FIG. 3, a schematic flow chart diagram presentation of a method in accordance with certain embodiments of the present invention. In block 300, a signal may be generated to activate an immobilizer included in an in vivo device. In some embodiments, such signal may originate from outside of the in vivo device and may be issued by for example a receiving system or a processor at controller connected with such receiving system, or by for example an operator or doctor who may view an image of an in vivo site or may otherwise receive information about an in vivo site that he wished to monitor for an extended period of time. In some embodiments, an operator may transmit a signal to for example a receiver in an in vivo device A receiver and for example a processor or controller with which such receiver is in contact, may generate a signal to activate an immobilizer in such in vivo device to immobilize the in vivo device. In some embodiments a signal may be generated in response to for example in vivo conditions detected by an in vivo sensor, and without input from an external operator. For example, a sensor may detect the presence of for example blood in the GI tract. The sensor's detection of blood may trigger a controller to activate an immobilization unit connected to the in vivo device. In some embodiments, a signal may include a burn of a fuse that holds a spring to which is connected an anchor or pointed head that may be included in an immobilization unit. Other signals and other methods or sources of generating signals are possible.

In block 302, an in vivo device may be immobilized in an area that is near, proximate to or in the vicinity of an in vivo site to be monitored For example, an immobilizing unit of an in vivo device that detected blood in a GI tract may immobilize the in vivo device in the area where the blood was detected. The in vivo device may continue to monitor the site or area for continued bleeding. In another example, an operator may view an image of an in vivo area that is generated by an in vivo device. If the image reveals an object, condition or area that the operator wishes to continue monitoring, the immobilizer may be activated and the device may be immobilized in the area proximate to the object or condition to be monitored. In some embodiments, the immobilizer may bring anchors with, for example, pointed heads into contact with, or may puncture, an endo-luminal tissue or wall to immobilize the in vivo device. One or more springs may propel the anchors to contact, grasp or puncture an endo-luminal tissue. Other methods of immobilizing an in vivo device are possible. In some embodiments, a signal may include a burn of a fuse that holds a spring to which may be connected an anchor or pointed head.

In block 304, the in vivo site, area or object may be monitored by the immobilized in vivo device. For example, an in vivo imaging device may capture images of an area or object over the period of time during which the in vivo device remains immobilized at a particular site. In some embodiments, an anchor or pointed head may include or contain a compound such as for example a drug that may be injected into or brought into contact with an endo-luminal tissue in the area where the in vivo device is immobilized. In some embodiments, anchors or grippers of the immobilization unit may remove a sample of tissue as part of for example a biopsy of an in vivo area. In some embodiments, anchors or pointed heads may be constructed of a material that degrades over time once exposed to in vivo conditions. Once the pointed heads degrade or melt, the in vivo device may be freed to continue moving through the body lumen While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. An autonomous in vivo sensing device comprising:
    a sensor;
    a degradable immobilizer; and
    a processor internal to the device to control said immobilizer attached to the device, said sensor to collect data relating to an in-vivo environmental condition while said sensing device passively traverses the gastrointestinal tract, said sensing device to transmit said data to said processor, wherein said processor is to issue a signal triggered in response to said sensor sensing data related to a change in the environmental condition, wherein said signal issued by said internal processor within the device activates said immobilizer attached to the device to stop the passive motion of the device.

2. The device as in claim 1, wherein said immobilizer is capable of degrading upon exposure to in vivo conditions.

3. The device as in claim 1, wherein said sensor comprises an imager.

4. The device as in claim 1, wherein said immobilizer comprises an anchor.

5. The device as in claim 4, wherein said anchor is a pointed anchor.

6. The device as in claim 1, wherein said immobilizer comprises a spring.

7. The device as in claim 6, wherein said spring is releasably attached to a fuse.

8. The device as in claim 1, wherein said immobilizer comprises a composition delivery unit.

9. The device as in claim 8, wherein said composition comprises a drug.

10. The device as in claim 1, comprising a power source.

11. An autonomous in vivo capsule comprising:
a sensor;
a degradable immobilization unit; and
a processor internal to the capsule to control said immobilization unit attached to the capsule, said sensor to collect data relating to an in-vivo environmental condition while said capsule passively traverses the gastrointestinal tract, said capsule to transmit said data to said processor, wherein said processor is to issue a signal in response to said sensor sensing data related to a change in the environmental condition, wherein said signal issued by said internal processor within the capsule activates said immobilization unit attached to the capsule to stop the passive motion of the capsule.

12. The capsule as in claim 11, comprising an anchor.

13. The capsule as in claim 11, said sensor comprising an imager.

14. A method of monitoring an in vivo site, the method comprising:
sensing, in an in-vivo device, data relating to an in-vivo environmental condition while said device passively traverses the gastrointestinal tract;
issuing a signal in response to said sensed data related to a change in the environmental condition, said signal issued by an internal processor disposed within the device to activate a degradable immobilizer attached to the in-vivo device;
immobilizing said device proximate to an in vivo site to be monitored in response to issuing said signal to stop the passive motion of the device; and
monitoring said in vivo site with said device.

15. The method as in claim 14, wherein said immobilizing comprises bringing an immobilizer into contact with an endoluminal tissue.

16. The method as in claim 14, wherein said immobilizing comprises releasing a spring holding said immobilizer.

17. The method as in claim 16, wherein said releasing a spring comprises burning a fuse holding said spring.

18. The method as in claim 14, comprising releasing a composition into said in vivo site.

19. The method as in claim 14, comprising freeing said device from said in vivo site.

20. The method as in claim 19, wherein said freeing comprises degrading an immobilizer.

21. The method as in claim 14, wherein said immobilizing said device comprises transiently immobilizing said device.

22. The method as in claim 14, wherein said monitoring comprises capturing images of said in vivo site.

23. A method for immobilizing an autonomous in vivo device comprising:
sensing, at an in-vivo device, data relating to an in-vivo environmental condition while said device passively traverses the gastrointestinal tract;
issuing a signal triggered in response to said sensed data related to a change in the environmental condition, said signal issued by an internal processor within the device to activate a degradable immobilizer attached to said in-vivo device to stop the passive motion of the device.

24. The method as in claim 23, comprising immobilizing said device proximate to an in vivo site to be monitored.

25. An in vivo sensing system comprising:
an immobilizable housing;
a sensor internal to said housing to collect data relating to in-vivo environmental condition while said housing passively traverses the gastrointestinal tract; and
a controller internal to said housing to issue a signal in response to data from the sensor indicating a change in the environmental condition, wherein said signal is issued by said internal controller within said housing to activate a degradable immobilization unit attached to said housing to stop the passive motion of the housing.

26. The system as in claim 25, wherein said sensor is an imager.

27. The system as in claim 25, wherein said immobilization unit comprises a pointed anchor.

28. The system as in claim 25, comprising a transmitter.

* * * * *